US010267733B2

(12) United States Patent
Van Dorpe et al.

(10) Patent No.: US 10,267,733 B2
(45) Date of Patent: Apr. 23, 2019

(54) SEMICONDUCTOR DEVICE FOR DETECTING FLUORESCENT PARTICLES

(71) Applicant: IMEC VZW, Leuven (BE)

(72) Inventors: Pol Van Dorpe, Spalbeek (BE); Liesbet Lagae, Leuven (BE); Peter Peumans, Herfelingen (BE); Andim Stassen, Leuven (BE); Philippe Helin, Leefdaal (BE); Bert Du Bois, Blanden (BE); Simone Severi, Leuven (BE)

(73) Assignee: IMEC VZW, Leuven (BE)

( * ) Notice: Subject to any disclaimer, the term of this patent is extended or adjusted under 35 U.S.C. 154(b) by 135 days.

(21) Appl. No.: 15/312,116

(22) PCT Filed: May 22, 2015

(86) PCT No.: PCT/EP2015/061479
§ 371 (c)(1),
(2) Date: Nov. 17, 2016

(87) PCT Pub. No.: WO2015/177373
PCT Pub. Date: Nov. 26, 2015

(65) Prior Publication Data
US 2017/0082544 A1     Mar. 23, 2017

(30) Foreign Application Priority Data
May 22, 2014   (EP) .................................. 14169507

(51) Int. Cl.
*G01N 21/64* (2006.01)
*G01N 21/77* (2006.01)

(52) U.S. Cl.
CPC ....... *G01N 21/6428* (2013.01); *G01N 21/648* (2013.01); *G01N 21/6454* (2013.01); *G01N 21/7703* (2013.01); *G01N 2201/0873* (2013.01)

(58) Field of Classification Search
CPC ............. G01N 21/648; G01N 21/6248; G01N 21/7743; G01N 33/54373
See application file for complete search history.

(56) References Cited

U.S. PATENT DOCUMENTS 6,287,871 B1 * 9/2001 Herron ............... G01N 21/6452
                                                     422/82.08
2003/0030814 A1 * 2/2003 Osinski .................. G01C 19/72
                                                        356/461

(Continued)

FOREIGN PATENT DOCUMENTS

WO      2014/031157 A1    2/2014

OTHER PUBLICATIONS

PCT International Search Report and Written Opinion, PCT International Application No. PCT/EP2015/061479 dated Aug. 19, 2015, 15 pages.

(Continued)

*Primary Examiner* — Dale E Page
*Assistant Examiner* — Quovaunda Jefferson
(74) *Attorney, Agent, or Firm* — McDonnell Boehnen Hulbert & Berghoff LLP (57) ABSTRACT

The present disclosure relates to semiconductor devices for detecting fluorescent particles. At least one embodiment relates to an integrated semiconductor device for detecting fluorescent tags. The device includes a first layer, a second layer, a third layer, a fourth layer, and a fifth layer. The first layer includes a detector element. The second layer includes a rejection filter. The third layer is fabricated from dielectric material. The fourth layer is an optical waveguide configured and positioned such that a top surface of the fourth layer is illuminated with an evanescent tail of excitation light guided by the optical waveguide when the fluorescent tags are present. The fifth layer includes a microfluidic channel. The optical waveguide is configured and positioned (Continued)

such that the microfluidic channel is illuminated with the evanescent tail. The detector element is positioned such that light from activated fluorescent tags can be received.

20 Claims, 7 Drawing Sheets

(56) References Cited

U.S. PATENT DOCUMENTS

| | | | |
|---|---|---|---|
| 2007/0223000 A1* | 9/2007 | Gahan | G01D 5/266 356/454 |
| 2010/0055666 A1 | 3/2010 | Wimberger-Friedl et al. | |
| 2011/0112769 A1* | 5/2011 | Niederberger | G01N 21/648 702/1 |
| 2013/0142477 A1* | 6/2013 | Diemeer | G01N 21/648 385/12 |

OTHER PUBLICATIONS

Blanco, F J et al., "Microfluidic-Optical Integrated CMOS Compatible Devices for Label-Free Biochemical Sensing", Journal of Micromechanics and Microengineering, vol. 16, 2006, pp. 1006-1016.

Duval, Daphne et al., "Grating Couplers Integrated on Mach-Zehnder Interferometric Biosensors Operating in the Visible Range", IEEE Photonics Journal, vol. 5, No. 2, Apr. 2013, pp. 9 pages.

* cited by examiner

SEMICONDUCTOR DEVICE FOR DETECTING FLUORESCENT PARTICLES

CROSS-REFERENCE TO RELATED APPLICATION

The present application is a national stage entry of PCT/EP2015/061479 filed May 22, 2015, which claims priority to European Patent Application No. 14169507.2 filed on May 22, 2014, the contents of each of which are hereby incorporated by reference.

FIELD OF THE INVENTION

The disclosure relates to a device for detecting particles. In particular, the disclosure relates to semiconductor devices for detecting biological particles including DNA, RNA, proteins, viral particles and cells based on fluorescence.

BACKGROUND OF THE INVENTION

Fluorescence detectors are sensitive detectors allowing analysis or detection of particles, such as biological molecules. A fluorescent detection is performed, for instance, on fluorescent tags attached to biological molecules, enabling the identification of specific biological molecules in a sample. However, some fluorescent detectors contain different components which cannot be fabricated using a semiconductor process flow.

There is a need for a compact fluorescence based detector that can be completely manufactured using semiconductor manufacturing processes.

SUMMARY

Some embodiments may provide a compact fluorescence detector which can be completely manufactured using semiconductor manufacturing processes.

Some embodiments may provide methods to manufacture waveguide structures using semiconductor manufacturing processes, more specifically CMOS compatible manufacturing processes.

This object is met by the device and method according to the independent claims. The dependent claims relate to example embodiments.

According to a first aspect, the present disclosure provides integrated semiconductor devices for detecting fluorescent tags is presented. The device comprises: a first layer comprising a detector element; a second layer located on top of the first layer, comprising a rejection filter; a third layer located on top of the second layer, fabricated from a dielectric material; a fourth layer located on top of the third layer, comprising an optical waveguide. The optical waveguide is configured and positioned such that a top surface of the fourth layer is illuminated with an evanescent tail of excitation light guided by the optical waveguide for activating the fluorescent tags when present on top of the fourth layer. The rejection filter is positioned such that fluorescence from the activated fluorescent tags is filtered before falling onto the detector element. The rejection filter is configured to reject the wavelength range of the excitation light and configured to transmit the wavelength range of fluorescence from the activated fluorescent tags. The detector element is positioned such that light is received from the activated fluorescent tags. The rejection filter is positioned such that fluorescence from the activated fluorescent tags is filtered before falling onto the detector element, wherein the rejection filter is configured to reject the wavelength range of the excitation light and configured to transmit the wavelength range of fluorescence from the activated fluorescent tags; and wherein the detector element is positioned such that light from the activated fluorescent tags can be received.

The device furthermore may comprise a fifth layer located on top of the fourth layer comprising a microfluidic channel, wherein the optical waveguide is further configured and position such that the microfluidic channel is illuminated with the evanescent tail.

The integrated semiconductor device wherein between the fourth layer and the fifth layer, a cladding layer is provided.

The integrated semiconductor device may, at a sensing region where interaction between the radiation and the fluorescent tags may occur, comprise a cladding layer that is patterned so as to have a reduced thickness or be locally absent.

In between the fourth layer and the cladding layer, a protective layer may be present. According to example embodiments, the protective layer may act as a passivation layer and/or may act as an etch stop layer during production of the device.

At a sensing region where interaction between the radiation and the fluorescent tags may occur, the protective layer may have been locally removed.

According to example embodiments, the integrated semiconductor device further comprises a fifth layer located on top of the fourth layer, comprising a microfluidic structure. The optical waveguide is further configured and positioned such that the microfluidic structure is illuminated with the evanescent tail of the excitation light guided by the optical waveguide. The detector element is positioned such that light originating from the illuminated microfluidic structure can be received.

According to different embodiments, the waveguide may be locally in direct contact with the sample region and thus the sample to be measured, with a thin layer, e.g. an etch stop layer, that acts as cladding layer, or with the full cladding layers. Whereas the distance between the waveguide and the sample should in most embodiments be as short as possible, in some embodiments the use of an intermediate thin layer may assist in optical interaction.

According to example embodiments, the first, second, third and fourth layers are comprised in a CMOS chip. The fifth layer is comprised in a fluidic substrate which is bonded to the CMOS chip.

According to example embodiments, the integrated semiconductor device further comprises: a grating coupler optically coupled to the optical waveguide for coupling an excitation light signal into the optical waveguide and a mirror positioned such that incoming excitation light is reflected towards the grating coupler. According to an embodiment of the disclosure, the mirror is positioned perpendicular to the direction of the incoming excitation light.

According to example embodiments, the optical waveguide comprises a single mode waveguide optically coupled to a multimode waveguide via a taper, and a grating coupler is optically coupled to the single mode waveguide.

According to example embodiments, the detector element comprises a spectral filter positioned such that light from the activated fluorescent tags is filtered before falling onto the detector element.

According to example embodiments, the integrated semiconductor device further comprises a non-continuous metal layer positioned in between the second and the fourth layer.

The non-continuous metal layer comprises at least one a gap positioned thereby allowing light from the activated fluorescent tags to reach the detector element. According to an embodiment of the disclosure, the non-continuous metal layer is absorbent.

According to example embodiments, the integrated semiconductor device further comprises at least one baffle positioned such that light from the activated fluorescent tags is redirected towards the detector element. According to an embodiment of the disclosure, the at least one baffle is absorbent. According to an embodiment of the disclosure, the at least one baffle is a cavity.

According to some embodiments, the optical waveguide is passivated or coated with $Al_2O_3$ for reducing scattering of the optical waveguide.

According to example embodiments, the optical waveguide forms a wall of the microfluidic structure.

According to example embodiments, a biological layer configured to bind particles of interest is located on top of the fourth layer whereby the biological layer is in direct contact with a fluid sample when present in the microfluidic structure or on the top surface of the fourth layer.

According to a second aspect, the present disclosure provides microchips comprising a plurality of integrated semiconductor devices as described in the first aspect of the disclosure wherein at least the optical waveguide is shared by the plurality of integrated semiconductor devices.

According to a third aspect, the present disclosure provides ELISA multi-well plates, characterized in that: each well comprises an integrated semiconductor device according to any of the embodiments described in the first aspect of the disclosure.

According to a fourth aspect, the present disclosure provides methods for fabricating a waveguide structure, the method comprising:
  providing at least one waveguide over or in a bottom cladding layer;
  providing a protective layer on the at least one waveguide;
  depositing an upper cladding layer over the protective layer;
  etching a cavity or opening in the upper cladding layer in a section comprising the at least one waveguide, whereby the protective layer acts as an etch stopping layer resulting in an exposed part of the protective layer.

According to some embodiments, the protective layer and the upper cladding layer can be selectively etched with respect to each other.

In some embodiments, the exposed part of the protective layer is the part covering the at least one at least one waveguide.

According to example embodiments, the etched cavity or opening has a geometry corresponding to a region comprising the at least one waveguide.

According to example embodiments, the waveguide structure is provided on a substrate, whereby the bottom cladding layer is disposed on the substrate. In example embodiments, the substrate comprises silicon, silicon dioxide, aluminum oxide, sapphire, germanium, gallium arsenide (GaAs), an alloy of silicon and germanium, indium phosphide (InP), silicon on insulator (SOI), or any other suitable material.

Some embodiments provide a method for fabricating a waveguide, for example a silicon nitride ($Si_xN_y$) waveguide in for example a silicon nitride ($Si_xN_y$) photonic platform, whereby the method is CMOS compatible. Moreover, some embodiments of the method may provide easiness of integration and compatibility with CMOS flow for high volume fabrication in CMOS foundry. In addition, embodiments of a method enable controlled process steps that can be transferred from one device to another.

A method may be provided for accurately removing an upper cladding layer of photonic devices comprising at least one waveguide, e.g. for creating an interaction region for radiation in a waveguide with a sample positioned above the waveguide, e.g. directly above the waveguide.

An etch stopping layer may be provided, resulting in a well-controlled process, whereby the upper cladding layer is etched in a controlled manner such that etching of the waveguide or bottom cladding layer, while etching the upper cladding layer, is avoided.

According to some embodiments, each waveguide may comprise, optionally longitudinal, sidewall surfaces, an optionally longitudinal top surface, and an optionally longitudinal bottom surface, whereby the optionally longitudinal bottom surface is disposed on the bottom cladding layer and the protective layer is disposed on the sidewalls and top surfaces.

According to some embodiments, the etching of a cavity in the upper cladding layer is performed by providing a photoresistive mask layer on the upper cladding layer and dry etching the photoresistive mask layer and upper cladding layer up to the preventing layer. In example embodiments, the dry etching comprises a two-step etching processes, such as an isotropic and anisotropic dry etch step. More specifically, first the photoresistive mask layer is anisotropically etched thereby exposing a part of the upper cladding layer, whereby in a second step the exposed upper cladding layer is isotropically etched up to the protective layer which acts as a stopping layer for the etchant. Whereby the etchant material applied is highly selective to the protective layer, for example alumina, resulting in that the protective layer acts as a stopping layer or highly resistant layer for the etchant materials.

According to some embodiments, the method further may comprise a further etching step, the further etching step comprising etching the exposed part of the protective layer selective to the waveguide. According to some embodiments, the further etching step may be performed by wet etching the protective layer and removing the latter selective to the materials of the waveguide and optionally other cladding layer.

Even though the cladding layer may be etched in the section where the waveguide is to get into contact with the sample, the upper and bottom cladding layers may remain as a part of the waveguide structure to reduce scattering loss and increase coupling.

The top surface and side walls of the at least one waveguide may be free of any cladding residues or residues resulting from the protective layer. As a result, particles (in a gas or liquid phase) which are brought in direct contact with the at least one waveguide, are sensed correctly without any signals due to any residual materials on the at least one waveguide.

The at least one waveguide may be free of any residues (from cladding or the protective layer) without any damage to the at least one waveguide.

According to some embodiments, the upper and bottom cladding layer is an oxide layer, for example a silicon oxide layer. In example embodiments, the bottom cladding layer is a dielectric layer. According to some embodiments, the bottom cladding layer, e.g. a dielectric layer, may have for example a thickness ranging from 0.2 μm to 1 μm. In some embodiments the bottom cladding layer may have a thickness greater than 0.5 μm in some other embodiments. The bottom cladding layer may have a refractive index (RI) in a range ranging from 1.2 to 1.5 and may also comprise silicon dioxide or a low-k dielectric material in some embodiments.

According to some embodiments, the protective layer material is chosen such that the material is adapted to act as an etch stopping layer or a hard mask when etching the upper cladding layer, for example the protective layer may act as an etch stopping layer for an oxide etch.

According to some embodiments, the protective layer material is chosen such that it can be deposited in a conformal way over the at least one waveguide. Conformal films may be deposited by thin-film deposition methods, such as atomic layer deposition, chemical vapor deposition or plating.

According to some embodiments, the protective layer material has a thickness smaller than 40 nm.

According to example embodiments, the protective layer material can be removed or etched selectively with respect to the waveguide material and bottom cladding layer.

According to example embodiments, the protective layer material can be patternable and need not interfere with the functionality of a circuit and/or the light propagation in the at least one waveguides. The protective layer can thereby also be considered a dummy layer.

According to example embodiments, the at least one waveguide comprises silicon nitride ($Si_xN_y$) as a core material of the waveguide or a high-k dielectric according to alternative embodiments.

According to example embodiments, the protective layer is an alumina ($Al_2O_3$) layer.

Alumina may be used as a protective layer, which can be etched in a controlled manner, and is, for example, not realized by a timed etch (as for instance is the case when using SiN as a protective layer material).

According to example embodiments, the at least one waveguide and cladding comprise materials that may characterize the waveguide as a waveguide selected from the group consisting of a dielectric waveguide, a high index-contrast waveguide, and a single-mode waveguide.

According to example embodiments, the waveguide may be characterized by a cross-sectional geometry selected from the group consisting of ridge waveguide geometry, rib waveguide geometry, channel waveguide geometry, wire waveguide geometry, and strip-loaded waveguide geometry.

According to alternative embodiments, the bottom cladding layer may comprise at least one trench, whereby the at least one trench has a geometry corresponding to the at least one waveguide such that the at least one waveguide may be provided, e.g. fitted, in the at least one trench in the bottom cladding layer.

Embodiments of example methods according to the present invention can be used to manufacture a device according to embodiments of the first, second, and third aspects of the present disclosure.

According to a fifth aspect, the present disclosure provides devices obtained by using methods according to the fourth aspect.

According to a sixth aspect, the present disclosure provides devices, whereby the device comprises at least one waveguide provided on a bottom cladding layer, a non-continuous protective layer provided on the bottom cladding layer, and a non-continuous upper cladding layer provided on the protective layer, whereby the non-continuous protective layer and upper cladding layer are adapted to define an opening such that the at least one waveguide is free of residues on its top and side wall surfaces.

Particular aspects are set out in the accompanying independent and dependent claims. Features from the dependent claims may be combined with features of the independent claims and with features of other dependent claims as appropriate and not merely as explicitly set out in the claims.

These and other aspects will be apparent from and elucidated with reference to the embodiment(s) described hereinafter.

BRIEF DESCRIPTION OF THE DRAWINGS

Further features will become apparent from the examples and figures, wherein.

DETAILED DESCRIPTION OF THE INVENTION

The present disclosure will be described with respect to particular embodiments and with reference to certain drawings but the disclosure is not limited thereto but only by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice of the disclosure. Any reference signs in the claims shall not be construed as limiting the scope. In the different drawings, the same reference signs refer to the same or analogous elements.

Furthermore, the terms first, second, third and the like in the description and in the claims, are used for distinguishing between similar elements and not necessarily for describing a sequential or chronological order. The terms are interchangeable under appropriate circumstances and the embodiments described herein are capable of operation in other sequences than described or illustrated herein.

Moreover, the terms top, bottom, over, under and the like in the description and the claims are used for descriptive purposes and not necessarily for describing relative positions. The terms so used are interchangeable under appropriate circumstances and the embodiments described herein are capable of operation in other orientations than described or illustrated herein.

Furthermore, the various embodiments, even when referred to as "preferred" are to be construed as example manners in which the disclosure may be implemented rather than as limiting the scope of the invention.

The term "comprising", used in the claims or description, should not be interpreted as being restricted to the elements or steps listed thereafter; it does not exclude other elements or steps. Where an indefinite or definite article is used when referring to a singular noun e.g. "a" or "an", "the", this includes a plural of that noun unless something else is specifically stated. It may be interpreted as specifying the presence of the stated features, integers, steps or components as referred to, but does not preclude the presence or addition of one or more other features, integers, steps or components, or groups thereof. Thus, the scope of the expression "a device comprising A and B" should not be limited to devices consisting only of components A and B, rather with respect to the present invention, the only enumerated components of the device are A and B, and further the claim should be interpreted as including equivalents of those components.

It should be noted that the use of particular terminology when describing certain features or aspects should not be taken to imply that the terminology is being re-defined herein to be restricted to include any specific characteristics of the features or aspects of the invention with which that terminology is associated.

Throughout the description, reference is made to "particles". This may refer to biological particles such as biomolecules. In particular, this may refer to DNA, RNA, proteins, viral particles and cells.

Throughout the description, reference is made to "ELISA". This refers to an enzyme-linked immunosorbent assay using antibodies and color change to identify a substance.

Throughout the description, reference is made to "non-continuous layers". This refers to layers which are interrupted spatially, therefor providing layers formed by at least two continuous sections next to each other with a gap or opening in-between.

Throughout the description, reference is made to "fluorescence". This refers to particles of a sample being excited by illumination, causing them to emit light due to its interaction with the sample. Fluorescence can be applied on particles as is, as well as on particles which are fluorescently tagged or labelled in order to aid its identification in a sample. Throughout the description, reference is made to "etching". This refers to removing layers from a surface during fabrication or manufacturing. In etching, part or the surface may be protected from the etchant, e.g. the material responsible for the removal, by a "masking" material, which is adapted to resist the etching. If the etch is intended to make a cavity in a material, the geometry of the cavity, e.g. depth of the cavity, may be controlled using etching time and the etch rate. Removal of a top layer of a multilayer structure, may be done without damaging the underlying or masking layers, or in other words by selectively etching a top layer and thus not removing or damaging the underlying or masking layers. Some etches may undercut the masking layer and form cavities with sloping sidewalls. The distance of undercutting is called bias. Etchants with large bias are called isotropic, because they erode the substrate equally in all directions. Anisotropic etches alternatively produce sharp, e.g. vertical sidewalls, well-controlled features.

Embodiments provide integrated semiconductor devices which can be used for fluorescence detection. In embodiments where the device is used for fluorescence based detection, a sample comprising particles which are capable to emit fluorescence when illuminated are provided. This can be for instance an intrinsic feature of a particle or this can be a fluorescence tag bonded with a molecule which does not emit light when illuminated.

According to a first aspect embodiments provide devices comprising a first layer 101 comprising at least one detector element 107. The detector element 107 may be a photodiode. The first layer 101 may be a silicon support, e.g. a silicon wafer. The detector element 107 may be partly embedded in the first layer 101, located at a surface 119 of the first layer 101. The sensing side of the detector element 107 may form an even surface with the surface 119 of the first layer 101 wherein the sensing side of each detector element 107 faces away from the surface 119 of the first layer 101. The first layer 101 may further comprise electronic circuitry electrically connected to the at least one detector element 107. The electronic circuitry may be a transistor layer.

The device further comprises a second layer 102 located on top of the first layer 101, comprising a rejection filter. In between the first 101 and the second 102 layer, a dielectric layer may be present, e.g. a semiconductor oxide layer. The rejection filter may be an optical filter configured to reject a specific wavelength range. For example, the rejection filter may be configured to reject the wavelength range of an optical signal used to activate particles, for instance fluorescent tags of particles, so called an incident illumination or excitation beam. The rejection filter may further be configured to allow transmission of a transmitted signal, for instance fluorescence from fluorescent tags. The rejection filter may shield the detector elements 107 from an excitation signal used to interact with particles, for instance to activate fluorescent tags of particles, guided by an optical waveguide. Thus, detector elements 107 only receive light as a result of interaction with the particles, for example from activated fluorescent tags. Noise may be reduced and accurate sensing of the transmitted signal, like, for instance, fluorescence from tags of particles, can be achieved. The rejection filter may be a Bragg filter. The rejection filter may be fabricated from an absorbing material, for example an absorbing polymer.

The device further comprises a third layer 103 located on top of the second layer 102 and is fabricated from a dielectric material, for example an semiconductor oxide.

The device further comprises a fourth layer 104 located on top of the third layer 103. The fourth layer 104 comprises an optical waveguide. The optical waveguide is a waveguide suitable for guiding an optical signal for interacting with particles, for instance activating or exciting fluorescent tags. For example, the optical waveguide may be a silicon waveguide, e.g. $SiO_2$, or a Silicon Nitride waveguide, e.g. $Si_3N_4$. The optical waveguide may comprise a grating coupler for coupling an external excitation light signal into the optical waveguide. For example, the grating coupler may be configured to an optical signal generated by a laser into the optical waveguide. The third layer 103 may be located in between the second 102 and the fourth layer 104 and functions as a spacer between the rejection filter and the optical waveguide. The third layer 103 may have a minimum thickness of at least 1 μm. The minimum thickness of the third layer 103 may ensure that optical properties of the optical waveguide are not influenced by the rejection filter and may act as a buffer layer. The efficiency of the optical waveguide need not be reduced. The optical waveguide may be positioned such that a top surface 122 of the fourth layer 104 is illuminated with an evanescent tail of incoming light, for instance excitation light, guided by the optical waveguide, for illuminating particles present on that top surface 122. Hence, optical properties of the optical waveguide are chosen such that illumination of the top surface is possible with the evanescent tail of the excitation light guided by the optical waveguide.

Figure 1A:
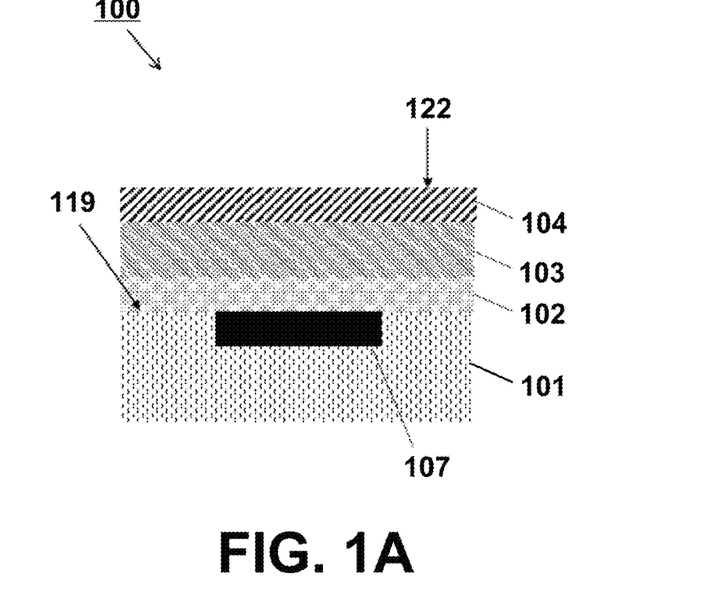
FIG. 1A schematically illustrates a cross-section of an integrated semiconductor device, according to example embodiments.

A fluid sample comprising particles may be provided on a top surface 122 of the fourth layer 104. The particles to be detected, present in the fluid sample, may be labelled with at least one fluorescent tag before providing them on the top surface 122 of the fourth layer 104. An optical signal is provided in the optical waveguide, for example by directing a laser beam on a grating coupler of the optical waveguide. An evanescent tail of the optical signal guided by the optical waveguide illuminates the top surface 122 of the fourth layer 104 thereby interacting with the particles and for instance activating fluorescent tags of particles present on that top surface 122. For example, the fluid sample may be in direct contact with the optical waveguide comprised in the fourth layer 104. This allows particles in the fluid sample to be located close to the excitation light. Efficient interaction with the particles, for instance activation of fluorescent tags of particles, can be achieved. After interacting with the particles a transmitting signal, resulting from for instance activated fluorescent tags which emit light, propagates through all layers present between the top surface 122 of the fourth layer 104 and the detector element 107 before being sensed by the detector element 107. FIG. 1A illustrates such an embodiment. A section through an integrated semiconductor device 100 in accordance with the present disclosure is shown. The substrate 101 comprises one detector element 107. The detector element 107 is located at a surface 119 of the substrate 101. A rejection filter 102 is located on top of the surface of the substrate 101, covering the sensing side of the detector element 107. A dielectric layer 103 is located on top of the rejection filter 102. An optical waveguide 104 is located on top of the dielectric layer 103. Particles of interest suitable for fluorescence detection may be provided on top of the top surface 122 of the fourth layer 104, e.g. in direct contact with the optical waveguide comprised in the fourth layer 104.

According to embodiments of the disclosure, the device further comprises a fifth layer 105 located on top of the fourth layer 104. Between the fourth 104 and the fifth layer 105, a spacing layer may be present, e.g. a semiconductor oxide layer. The fifth layer may comprise a microfluidic structure 106. The fifth layer may be considered as a fluidic substrate. The fifth layer may be fabricated from a semiconductor material, e.g. silicon, from a plastic, a polymer, PDMS, SU-8, glass or any other suitable material for microfluidic applications. The optical waveguide comprised in the fourth layer 104 is positioned such that an evanescent tail of the incoming light, for example excitation light, guided by the optical waveguide illuminates the microfluidic structure 106, e.g. illuminating the complete micro fluidic structure 106. Hence, in fluorescence mode, a fluorescent tag attached to a particle present in the microfluidic structure 106 may be activated by that evanescent tail of the excitation light. The direction of the optical waveguide may be perpendicular to the direction of the microfluidic structure 106. An optical waveguide may be used to illuminate different microfluidic structures. According to an embodiment of the disclosure, a plurality of devices 100 may be present wherein one optical waveguide may be used to interact with particles, for instance activate fluorescent tags present in different microfluidic structures 106. In some embodiments, the optical waveguide may be shared by the plurality of devices 100. This is further described in the section on the second aspect of the disclosure.

Figure 1B:
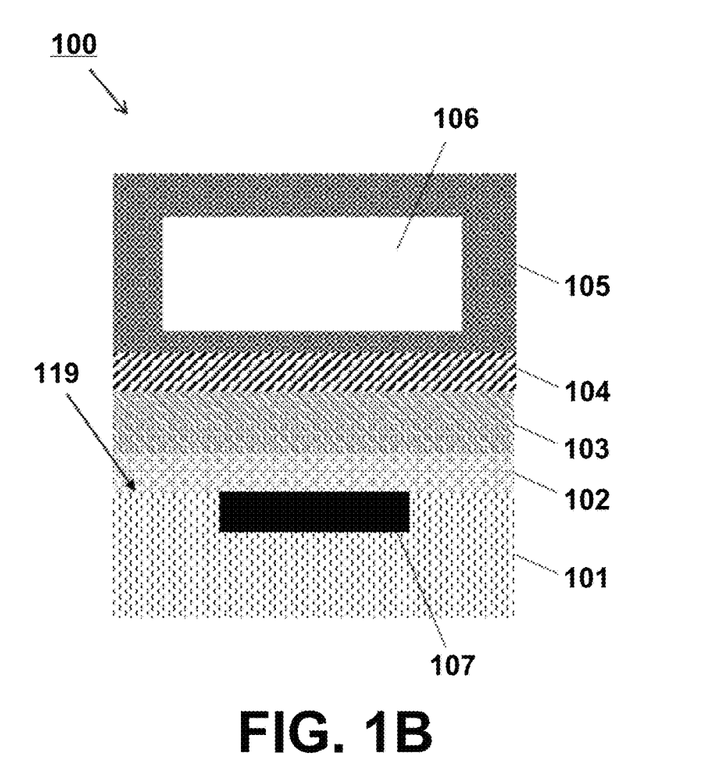
FIG. 1B schematically illustrates a cross-section of an integrated semiconductor device, according to example embodiments.

According to embodiments of the disclosure, the microfluidic structure 106 may be completely embedded in the fifth layer 105. In this arrangement, the fifth layer 105 is a closed fluidic substrate. The fifth layer 105 is adapted to enclose and contain a fluid sample, whereby the fluid sample in the microfluidic structure 106 may be in direct contact with the walls of the fifth layer 105. FIG. 1B illustrates such an embodiment. A section through an integrated semiconductor device 100 in accordance with the present disclosure is shown. The substrate 101 comprises one detector element 107. The detector element 107 is located at a surface 119 of the substrate 101. A rejection filter 102 is located on top of the surface of the substrate 101, covering the sensing side of the detector element 107. A dielectric layer 103 is located on top of the rejection filter 102. An optical waveguide 104 is located on top of the dielectric layer 103. A substrate 105 comprising a microfluidic structure 106 is located on top of the optical waveguide.

Figure 1C:
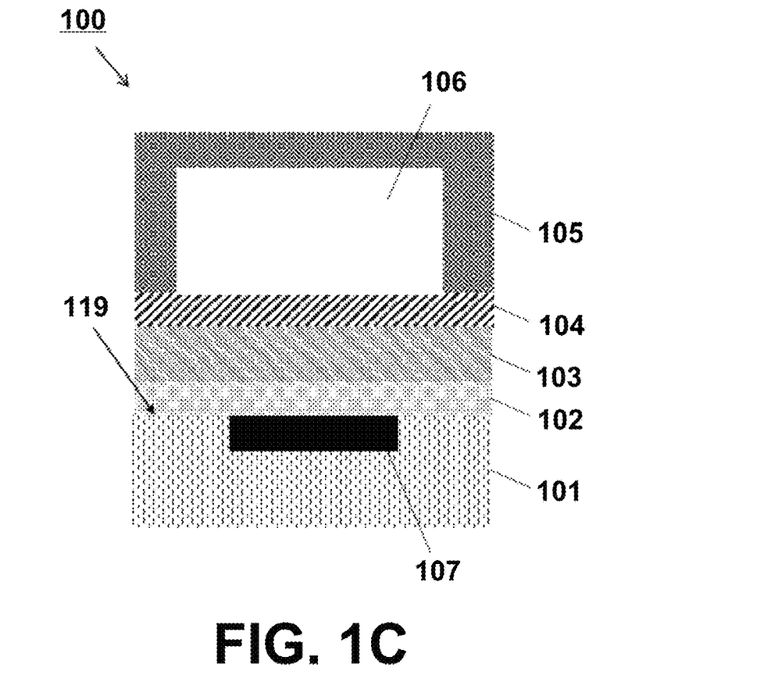
FIG. 1C schematically illustrates a cross-section of an integrated semiconductor device, according to example embodiments.

According to embodiments of the disclosure, the microfluidic structure 106 may be embedded in the fifth layer 105, wherein the fourth layer 104 forms at least a wall of the micro fluidic structure 106 and wherein the fourth layer 104 is in direct contact with a fluid sample inside the microfluidic structure 106. Thus, the optical waveguide may act as a wall of the microfluidic structure 106. The optical waveguide may be in direct contact with a fluid sample present in the microfluidic structure 106. This allows particles in the fluid sample to be located close to the incident, for instance excitation, light guided by the optical waveguide. In some embodiments, efficient interaction with particles, for instance, activation of fluorescent tags of particles, can be achieved. Such an embodiment is illustrated in FIG. 1C.

Figure 1D:
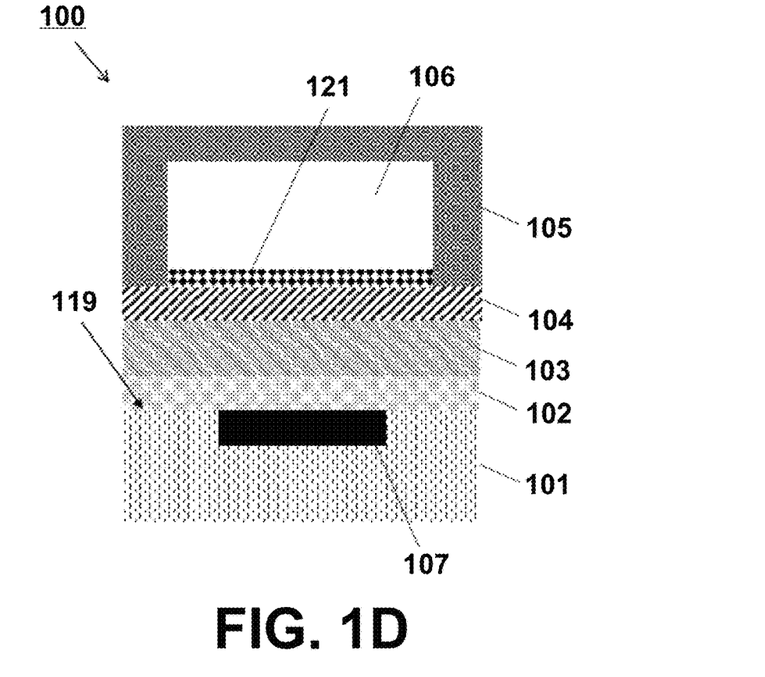
FIG. 1D schematically illustrates a cross-section of an integrated semiconductor device, according to example embodiments.

The fourth layer 104 may further comprise a biological layer 121 for binding particles of interest. The biological layer 121 may be in direct contact with a fluid sample in the microfluidic structure 106 and may comprise receptors configured to bind particles of interest as well as blocking agents to avoid binding particles not of interest. Such an embodiment is illustrated in FIG. 1D.

A fluid sample comprising particles may be provided in the microfluidic structure 106. The particles to be detected, present in the fluid sample, may be labelled with at least one fluorescent tag before providing them in the microfluidic structure 106. If the microfluidic structure 106 is a microfluidic channel, the fluid sample is propagated through the microfluidic channel. A microfluidic pump fluidly connected to the microfluidic channel may be used for such purposes, e.g. a capillary pump for creating a pressure inside the microfluidic channel. The use of a capillary pump may lower the total cost of the device. An optical signal is provided in the optical waveguide, for example by directing a laser beam on a grating coupler of the optical waveguide 104. An evanescent tail of the optical signal guided by the optical waveguide 104 illuminates the microfluidic structure 106 thereby interacting with particles, for instance activating fluorescent tags of particles. The illuminated particles, for instance activated tags emit light which propagates through all layers present between the microfluidic structure 106 and the detector element 107 before being sensed by the detector element 107.

It will be appreciated that, although only one detector element 107 is shown in FIG. 1, different configurations are possible, for example a plurality of detector elements 107 may be present sensing light from the same microfluidic structure 106. In embodiments where one type of fluorescent tags is used, the use of a single detector element may be appropriate. When for instance different types of fluorescent tags are used, multiplexed detection of tags may be realized by using multiple detector elements. By tagging different types of particles with different types of fluorescent tags, multiplexed detection of different types of particles, for instance bioparticles may be realized by using multiple detector elements.

According to embodiments of the disclosure, the fifth layer 105 may comprise an indentation, e.g. a nanopore. The indentation may be a nano-sized hole through the fifth layer 105 and down to the fourth layer 104. The indentation may comprise a means for translocating a biomolecule, e.g. a means for translocating DNA. The means for translocating a biomolecule may have a biological nature, e.g. an enzyme.

According to an embodiment of the disclosure, the fifth layer 105 is a structured layer. The structures of the layer may increase the confinement of the particle/light combination. The fifth layer 105 may be a dielectric layer. Using a dielectric material may reduce absorption losses compared to the use of other materials and may improve compatibility with CMOS processing.

The devices according to embodiments of the present disclosure may be manufactured using CMOS compatible processing steps. For example, the first layer 101 may be a CMOS chip. The second 102, third 103 and fourth layer 104 may be layers created on the CMOS chip during a custom back-end of line process. The fifth layer 105 may be an open fluidic substrate which is bonded to the fourth layer 104 wherein the open fluidic substrate is closed by the fourth layer 104. This allows the fourth layer 104 to be in direct contact with a fluid sample present in the microfluidic structure 106 of the fifth layer 105.

According to an embodiment of the disclosure, the device 100 comprises a grating coupler which is optically coupled to the optical waveguide for coupling an incoming or incident light signal into the optical waveguide. The grating coupler may be located in the fourth layer 104. The device 100 may further comprises a mirror which is positioned such that an incoming light signal is reflected towards the grating coupler. The mirror may be a dielectric enhanced metal mirror. Such a mirror has a high reflectivity. The mirror may be a CMOS compatible metal layer, e.g. Al (400-700 nm), TiN (>600 nm) or Cu (>700 nm). The choice of the material depends on the emission wavelength of used fluorescent tags. The mirror may be positioned underneath the grating coupler. For example, the mirror is positioned underneath the surface of the grating coupler adjacent to the surface of the grating coupler which receives the transmitted light, in fluorescence mode the excitation light. Light falling onto the mirror (and not coupled into the optical waveguide) will be reflected towards the grating coupler. This increases the efficiency of the grating coupler. The mirror may be located in a dielectric layer located in between the detector element 107 and the rejection filter 102. Alternatively, the mirror may be located in the third 103 or the fourth layer 104. The mirror may be positioned such that the orientation of its reflective surface is perpendicular to the direction of an incoming excitation light signal, that is, the light signal which may be coupled into the optical waveguide. In such an arrangement, an incoming excitation light signal is reflected in a direction opposite to the direction of the incoming excitation light signal. In some embodiments, an incoming light signal is redirected away from the device. This avoids interference with any other component present on the device and may reduce noise. The use of a dielectric enhanced metal mirror may reduce noise even further.

According to an embodiment of the disclosure, the optical waveguide, providing an incident light for particles of a sample, comprises a single mode waveguide optically coupled to a multimode waveguide via a taper, e.g. an adiabatic taper. A fiber optic coupler may be optically coupled to the single mode waveguide. In such an arrangement, the multimode waveguide may be used to illuminate the top surface 122 of the fourth layer 104 or the microfluidic structure 106. Hence, the multimode waveguide may be positioned thereby allowing illumination of the top surface 122 of the fourth layer 104 or the microfluidic structure 106.

In some embodiments, multiple particles may be detected simultaneously. Simultaneous illumination of particles on the top surface 122 of the fourth layer 104 or in the microfluidic structure 106 may be achieved using a broad optical waveguide capable of illuminating the complete top surface 122 of the fourth layer 104 or the complete microfluidic structure 106. Such a broad optical waveguide may diminish light scattering in such a waveguide. However, to couple light into such a broad waveguide, a large grating coupler and consequently a broad excitation light beam may be needed. Such a broad light beam may interfere with other components of the device. Also, a large grating coupler may, has the disadvantage that due to the large number of periods of the etch, be very shallow and also have a narrow-banded response. In an example embodiment, a small grating coupler may be used which is optically coupled to a single mode waveguide. The single mode waveguide is then tapered to a multimode waveguide (broad waveguide). Some embodiments allow the use of a broad waveguide without large excitation light beams and large grating couplers. The small grating coupler can then be addressed by an optical fiber or a free-space beam.

According to an embodiment, the detector element comprises a spectral filter 108 positioned such that light originating from the top surface 122 of the fourth layer 104 or from the microfluidic structure 106 is filtered. The spectral filter 108 may be positioned in between the first 101 and the second layer 102. For example, the spectral filter 108 may be located on top of the first layer 101, covering the sensing side of the detector element 107. The spectral filter 108 may be embedded in a layer 120 present in between the first 101 and the second layer 102. The layer 120 may be an oxide layer which is used for planarization. For example, a spectral filter 108 may be created on top of the first layer 101. An oxide layer 120 may be deposited on top of the surface of the first layer 101. Thereafter, the oxide layer 120 may be smoothened or etched to create an even surface with a top surface of the spectral filter 108. The rejection filter can then be created upon the prepared surface.

Figure 2:
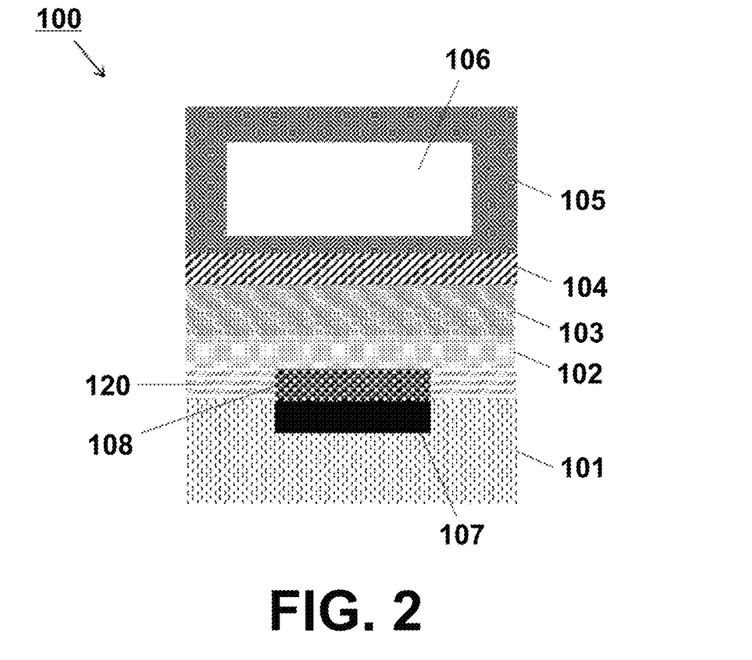
FIG. 2 schematically illustrates a cross-section of an integrated semiconductor device comprising a spectral filter, according to example embodiments.

Such an embodiment is illustrated in FIG. 2. The device 100 comprises one detector element 107 having a spectral filter 108 on top, covering its sensing side. The spectral filter 108 is located in a layer 120 in between the first 101 and the second layer 102.

According to an embodiment of the disclosure, at least two detector elements 107 are present in the first layer 101 wherein each detector element 107 is located at a surface 119 of the first layer 101. Each detector element 107 may comprise a different spectral filter 108. In other words, each detector element 107 may be covered by a different spectral filter 108 wherein the spectral filter 108 covers the sensing side of the detector element 107. Each spectral filter 108 may be configured to filter a different wavelength range of an optical signal. Some embodiments permit light with different wavelength ranges originating from the top surface 122 of the fourth layer 104 or from the microfluidic structure 106 to be detected by the device 100, simultaneously. For example, if different types of fluorescent tags are used for tagging different types of particles (each type of particle being tagged by a different type of fluorescent tag), each spectral filter may be configured to filter the wavelength range of one type of fluorescent tags. The use of different spectral filters allows detection of different types of particles in parallel.

Figure 3:
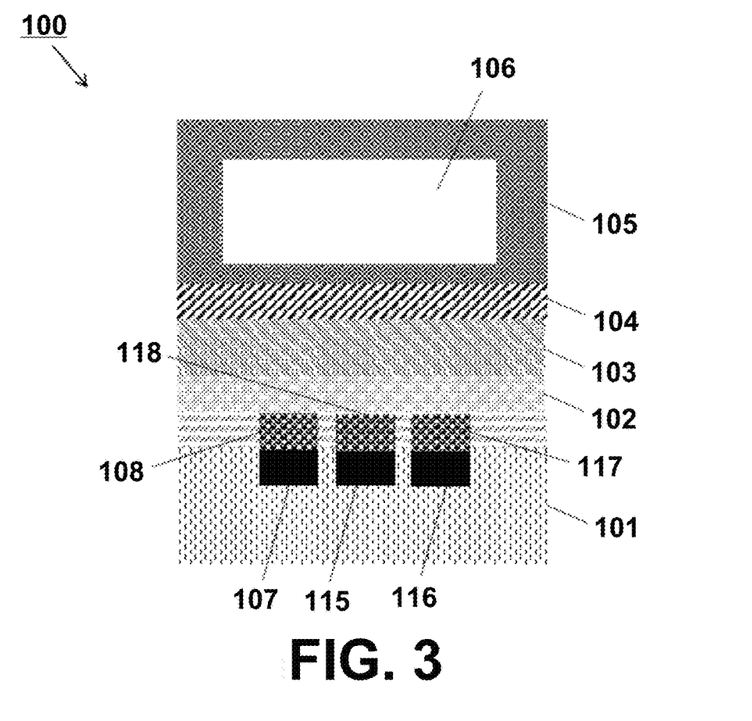
FIG. 3 schematically illustrates a cross-section of an integrated semiconductor device comprising multiple detector elements and spectral filters, according to example embodiments.

FIG. 3 illustrates an embodiment of the disclosure wherein three detector elements 107, 115, 116 are illustrated. Each detector element 107, 115, 116 comprises a spectral filter 108, 118, 117, positioned on top of the detector element 107, 115, 116. The spectral filters 108, 118, 117 are located in between the detector element 107, 115, 116 and the microfluidic structure 106 to filter transmitted light, e.g. light originating from that microfluidic structure 106 after illumination, before falling onto the detector elements 107, 115, 116. As in the previous embodiment each spectral filter 108, 118, 117 may be configured to filter a different wavelength range of an optical signal.

According to an embodiment of the disclosure, the device 100 further comprises a non-continuous metal layer 109 positioned in between the second 102 and the fourth layer 104. For example, the non-continuous metal layer 109 may be located within the third layer 103. The non-continuous metal layer 109 comprises a gap which is positioned thereby allowing light originating from the top surface 122 of the fourth layer 104 or from the illuminated part of the microfluidic structure 106 reaching the detector element 107. The gap may be filled with another material which allows light propagation. Thus, the propagation path of light originating from the top surface 122 of the fourth layer 104 or from the microfluidic structure 106 is not blocked by the non-continuous metal layer 109. The non-continuous metal layer 109 may be a light blocking layer. Thus, the non-continuous metal layer 109 may shield the detector element 107 from scattered light and auto fluorescence from the optical waveguide. This increases the signal to noise ratio of the device. The non-continuous metal layer 109 may be positioned at a distance from the optical waveguide to avoid disturbance of optical properties of the optical waveguide. This distance depends on the waveguide geometry and the used wavelength. For short wavelengths (<600 nm) or very confined (thick/wide) waveguides: >1 μm, longer wavelengths >(>600 nm) or less confined waveguides (narrow/thin): >2 μm. For example, the non-continuous metal layer 109 may be an absorbing metal layer. This absorbing property avoids reflection of light inside the device thereby further reducing noise.

Figure 4:
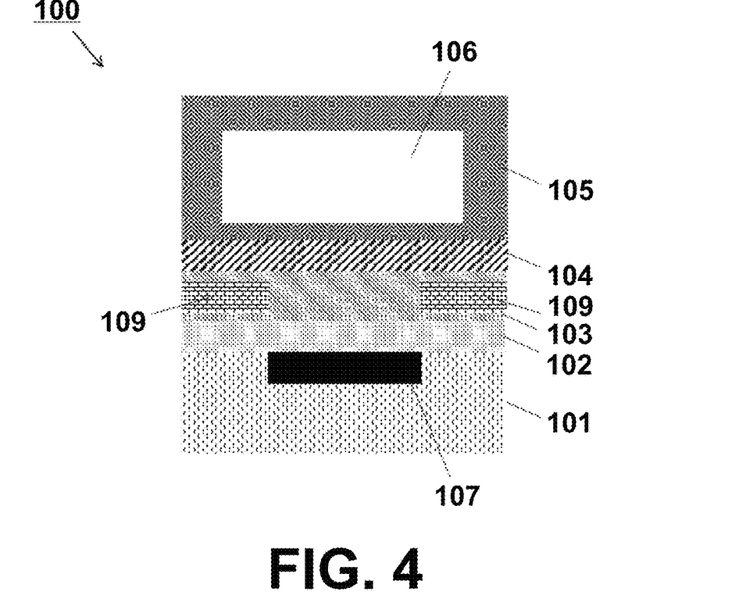
FIG. 4 schematically illustrates a cross-section of an integrated semiconductor device comprising a light blocking layer, according to example embodiments.

FIG. 4 illustrates an embodiment of the disclosure wherein the non-continuous metal layer 109 is located in the third layer 103 of the device 100. For example, the at least two sections of the non-continuous metal layer 109 may be located at both the sides within the third layer 103, providing at least a gap in-between. Whereby the at least one a gap is positioned such that light originating from the activated fluorescent tags is allowed to reach the at the least one detector element.

Figure 5:
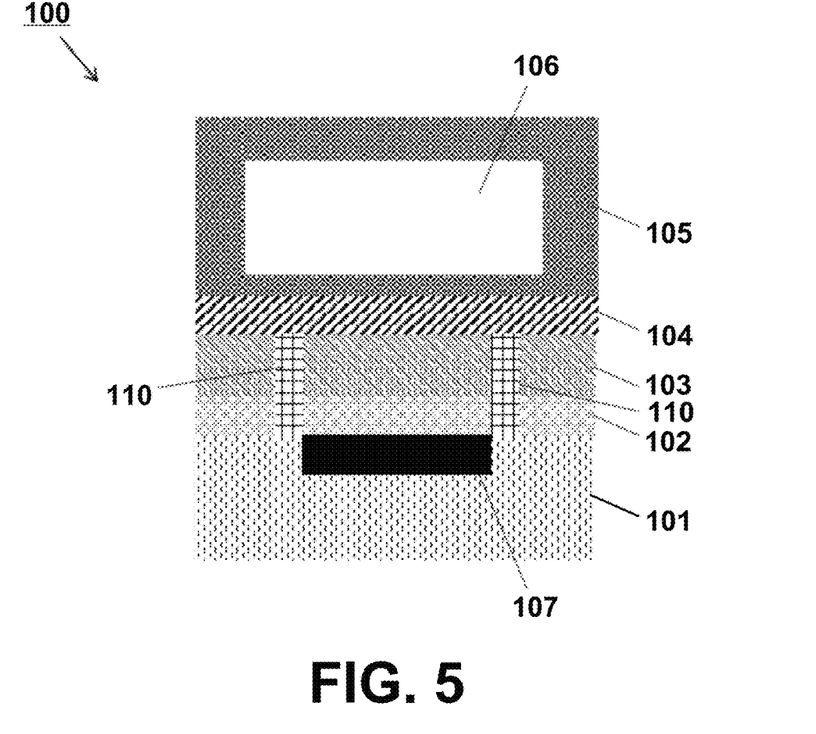
FIG. 5 schematically illustrates a cross-section of an integrated semiconductor device comprising baffles, according to example embodiments.

According to an embodiment, the device 100 further may comprise at least one baffle 110 positioned such that light originating from the top surface 122 of the fourth layer 104 or from the microfluidic structure 106 is redirected towards the detector element. The at least one baffle 110 may be located in between the first 101 and the fourth layer 104. According to an embodiment, the baffles 110 extend upwards from the first layer 101 into the second 102 and optionally also into third layer 103. The second layer 102 comprising the rejection filter is then formed between the baffles 110. The baffles 110 may be metallic baffles, e.g. aluminum baffles. Baffles 110 may be reflective or absorbent. In the former case, the baffles 110 reflect stray light onto the detector element 107, and in the latter case, the baffles 110 absorb stray light to prevent cross-talk. When multiple microfluidic structures 106 are present on the device, absorbent baffles 110 can be used to avoid cross-talk. That is, they ensure that photons emitted by a fluorescent tag are not sensed by detector element associated with another microfluidic structure. In a reflective implementation, each baffle 110 may comprise a cavity, e.g. a cavity formed within the third layer 103 and which has a different refractive index to that of the third layer 103 allowing emitted light to be reflected therefrom.

In an embodiment, the baffles can be replaced by grooves. A groove is etched to form a cavity into which a material layer is deposited, under certain conditions. These conditions are chosen such that growth of the material layer is stimulated to create a neck for pinching off the entrance of the cavity. In this way, the entrance to the cavity is filled with no material. Incident light will be reflected by each cavity and remain within the layer(s) in which the cavities are formed. Using this kind of structure, a light pipe is created towards the photon detectors, and light will be reflected by the cavities as the index of the air of the cavities is smaller than the index of the material of the layer in which the baffle is located. The use of such cavities provides an efficient way to reflect light in which the efficiency is 100%. The efficiency using metal baffles is lower and therefore less efficient.

According to an embodiment, the optical waveguide is a Silicon Nitride optical waveguide and comprises an Al2O3 coating (for example as an upper cladding layer). The effect of the coating may be a reduction of scattering loss in the optical waveguide. Scattered light of the optical waveguide as it may reach detector elements 107 thereby disturbing an optical signal originating from the top surface 122 of the fourth layer 104 or from the microfluidic structure 106 sensed by the detector elements 107. Hence, signal to noise ratio of the device may increase.

The device may be used for detecting biomolecules, proteins, DNA, RNA, vesicles, viruses, bacteria, cells. The device may also be used for obtaining fluorescence spectra of particles, like for instance biomolecules, proteins, DNA, RNA, vesicles, viruses, bacteria, cells.

Figure 6:
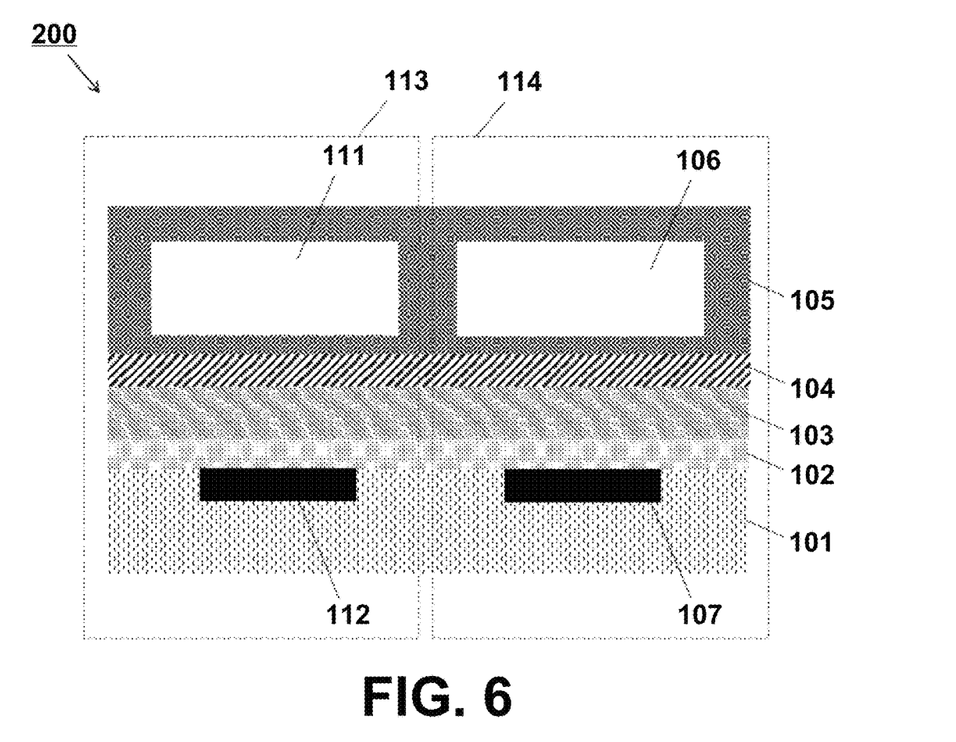
FIG. 6 schematically illustrates a cross-section of a microchip comprising two integrated semiconductor devices, according to example embodiments.

According to a second aspect of the present disclosure, microchips 200 are presented comprising a plurality of devices 100 as described in the first aspect of the disclosure. As a result, embodiments may provide microchip assays. Each device 100 of the microchip 200 may be referred to as a test cell. An embodiment of the second aspect of the disclosure is illustrated in FIG. 6. The microchip 200 comprises two test cells 113, 114, each test cell comprising a microfluidic structure 106,111. Each microfluidic structure 106, 111 may be associated with a different detector element 107, 112. Due to the layered structure of the microchip 200, different components of the test cells 113, 114 may be shared by different test cells 113, 114 of the microchip 200. In particular, the rejection filter may be shared by the different test cells 113, 114. This may reduce complexity of manufacturing, thereby reducing total cost. Further, the optical waveguide may be shared by the different test cells 113, 114. The optical waveguide may be used to simultaneously illuminate microfluidic structures 111, 106 of different test cells 113, 114. This may only require one light source to illuminate multiple microfluidic structures of different test cells 113, 114.

According to a third aspect, an ELISA multi-well plate is presented wherein each well contains an integrated semiconductor device as described in the first aspect of the disclosure. Thus, in each well an integrated semiconductor device according to an embodiment of the disclosure functions as a bottom wall of that well. In each well, a detection on the fluid sample present in that well may be performed in parallel.

The propagation of light trough waveguides in some photonic devices occurs due to a difference in refractive index of a material covering the waveguide and the waveguide material itself. In SiN waveguide circuits, the latter may be realized by providing, for example through deposition, a silicon oxide cladding on the bottom and on top of a silicon nitride ($Si_xN_y$) waveguide, resulting in that the waveguide is sandwiched or interposed between the bottom and top oxide cladding. However, as illustrated above for sensing applications, a part of the waveguide, more specifically the top surface of the waveguide, may be in direct contact with analyte molecules in a solution, whereby the solution is in a gas or liquid state. Therefore on some parts of the circuitry, e.g. the part comprising the waveguides, the top or upper cladding layer should be removed.

Figure 7A:
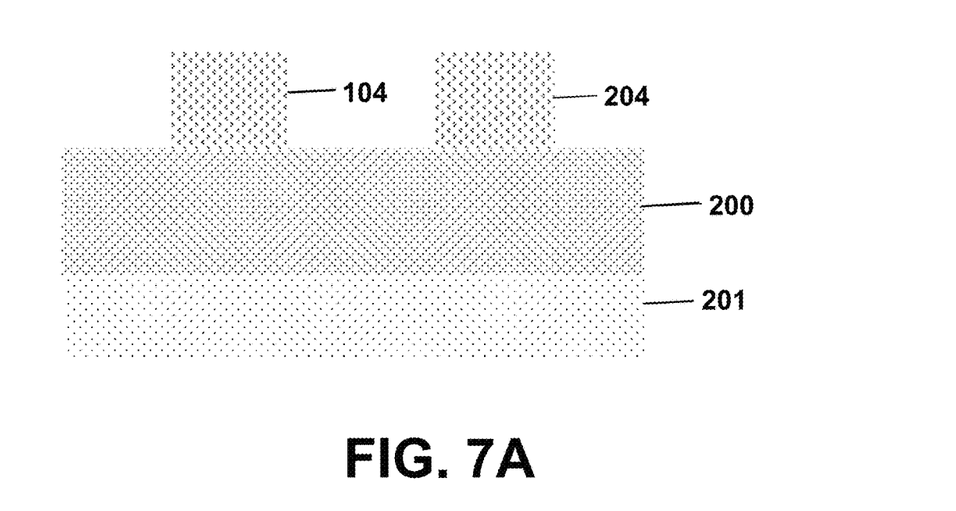
FIG. 7A schematically illustrates a method, according to example embodiments.
Figure 7B:
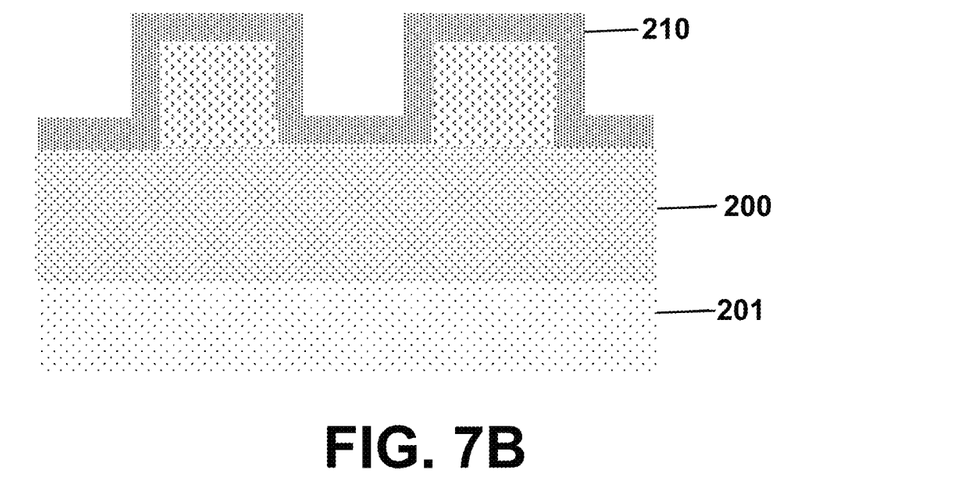
FIG. 7B schematically illustrates a method, according to example embodiments.

According to a fourth aspect, a method is presented for removing or opening the upper cladding layer of a photonic platform, for example a silicon nitride photonic platform. In addition, a method is presented for fabricating a waveguide structure, for example according to a first, second, and third aspect, as illustrated in FIGS. 7A-E. FIG. 7A illustrates providing at least one waveguide 104, 204 over a bottom cladding layer 200, for example silicon dioxide, whereby the bottom cladding layer is provided on a substrate 201, in the example of FIG. 7A this is a silicon substrate is illustrated. In embodiments according to a first, second and third aspect the bottom cladding layer 200 may relate to the third layer 103, which is a dielectric material, and a substrate 201 may for example comprise the first layer 101 comprising the detector element 107 and second layer 102 comprising the rejection filter. FIG. 7B further illustrates providing a protective layer 210 on the at least one waveguide 104, 204. In a specific embodiment, the at least two waveguides 104, 204 are deposited and may be patterned waveguides, for example patterned SiN waveguides, whereby the protective layer 210 may be an alumina ($Al_2O_3$) layer having a thickness smaller than 40 nm, which has been deposited, for example by atomic layer deposition, over the at least two waveguides 104, 204 covering the at least two waveguides in a uniform manner (e.g. as a blanket) or in a patterned manner. Patterning the protective layer, for example an alumina layer, may be performed using suitable methods, like for instance using a suitable photoresist mask layer (not shown). Some embodiments may obtain a patterned protective layer such that it is possible to remove certain areas of the protective layers, such that for example when grating couplers are provided on the at least one waveguides, the areas comprising the latter are exposed when the upper cladding layer is etched. In example embodiments, the protective layer need not impair the light propagation in the at least one waveguides. The protective layer is chosen, like for example for alumina, such that the refractive index falls between that of the cladding layer (for example $SiO_x$) and waveguide (for example SiN) material. In embodiments the protective layer is provided between the upper cladding layer and the at least one waveguide and the parts of the bottom cladding layer not comprising the at least one waveguide. The protective layer may be deposited by any suitable deposition technique, such as using atomic layer deposition, sputtering or evaporating techniques, a thin-film depositing technique is used such that a conformal layer is obtained.

Figure 7C:
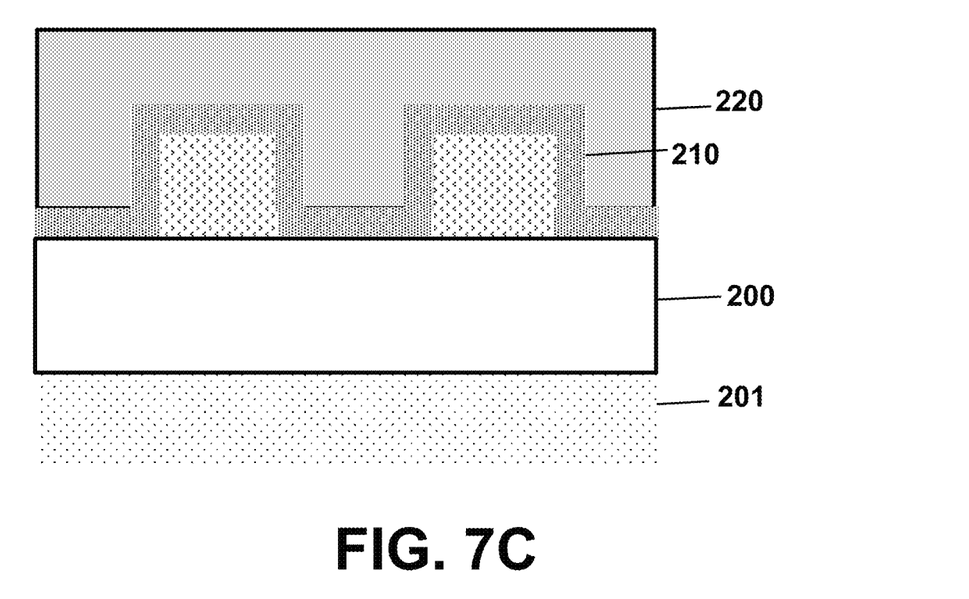
FIG. 7C schematically illustrates a method, according to example embodiments.
Figure 7D:
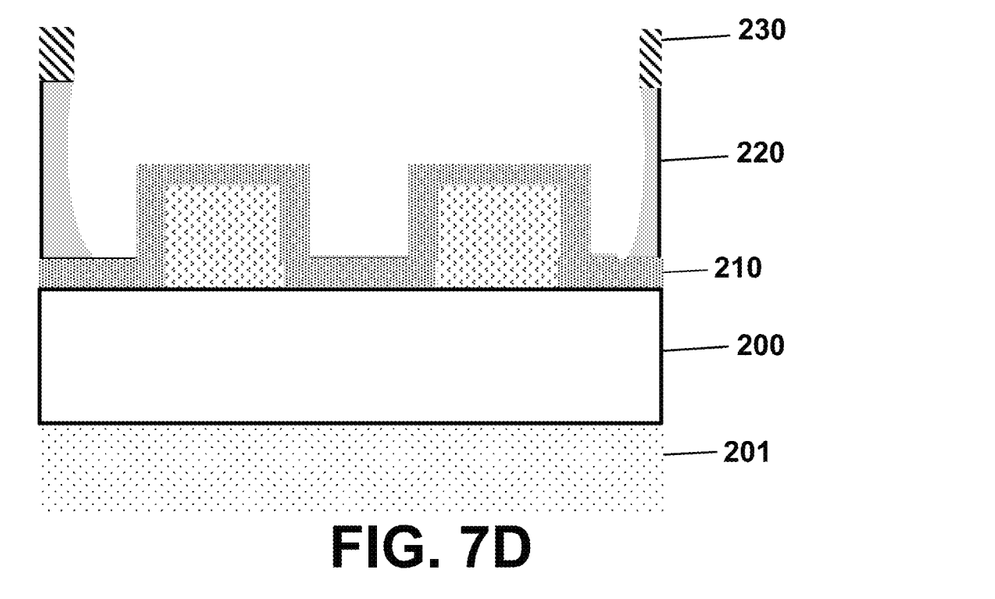
FIG. 7D schematically illustrates a method, according to example embodiments.
Figure 7E:
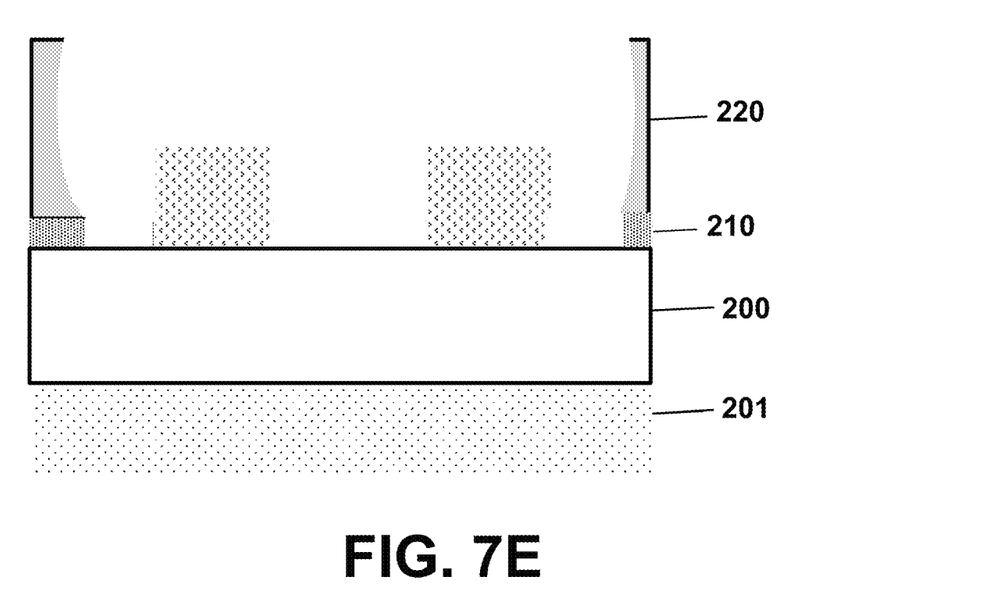
FIG. 7E schematically illustrates a method, according to example embodiments.

Any suitable materials which are adapted to fulfil all of the following properties, may be used as protective or dummy layer: (a) materials which are adapted to act as a hard mask or stopping layer for an oxide etch, (b) materials which can be deposited in a conformal way on the waveguide material, for example SiN, (c) materials which are removable selective to the waveguide material and the bottom cladding layer, and (d) materials which are patternable such that the latter can be removed from active circuit areas so as to not interfere with the functionality of the circuit. In example embodiments, alumina may be used as protective layer, silicon oxide ($SiO_x$) as upper and bottom cladding material and silicon nitride ($Si_xN_y$) as waveguide material. The presence of a thin alumina layer need not drastically reduce the functionality of the waveguides. In certain cases, the presence of a thin alumina layer may improve the functionality by decreasing the light propagation loses. In a next step, an upper cladding layer 220 is provided over the protective layer 210, as illustrated in FIG. 7C, whereby the upper cladding layer 220 may be planarized. Starting from the waveguide structure of FIG. 7 C a first etching is step is performed. Whereby the first etching step comprises etching a cavity in the upper cladding layer 220 whereby the protective layer 210 acts as a stopping layer for the first etching step resulting in an exposed part of the protective layer 210, more specifically the exposed part of the protective layer is the part covering the at least one at least one waveguide 104, 204. In example embodiments, the first etching step is a dry etching step. The dry etching step may comprise a two-step etching process performed on the waveguide structure of FIG. 7C whereby the waveguide structure further comprises a photoresist masking layer 230 provided over the upper cladding layer 220. The two-step etching process comprises for one example in a first step exposing the photoresist masking layer 230 to a plasma etchant, which may result in an anisotropic etching of the photoresist masking layer exposing the upper cladding layer 220. In a second step the exposed upper cladding layer 220 may be etched by an isotropic etching step, for example using fluorocarbon and sulfur hexafluoride based plasma etchants. These etchants, such as plasma etchants, are adapted to etch the upper cladding layer 220 but are selective to the protective layer 210, resulting in that the plasma etchants are stopped by the protective layer 210 and do not penetrate or act as etchants for the underlying waveguide materials or the bottom cladding material, as both are protected by the protective layer. As a result, plasma etchants which are for instance active for the waveguide material but highly selective or resistant for the protective layer can be used as etchants. In a last step, the method, according to embodiments, may comprise a further etching step, such as a wet etching step, whereby the exposed protective layer 210, which are the exposed parts or regions of the protective layer 210 which cover the at least one waveguides 104, 204, are etched. This last etching step is performed, selective to the waveguide material and the bottom cladding layer. In embodiments where alumina is used as a protective layer 210, an etchant which is adapted to etch alumina but which is selective, e.g. does not remove, the waveguide material, for instance SiN, and the bottom cladding layer 200 is used.

The invention claimed is:

1. An integrated semiconductor device for detecting fluorescent tags, comprising:
   a first layer, wherein the first layer comprises a detector element;
   a second layer located on top of the first layer, wherein the second layer comprises a rejection filter;
   a third layer located on top of the second layer, wherein the third layer is fabricated from a dielectric material;
   a fourth layer located on top of the third layer, wherein the fourth layer comprises an optical waveguide configured and positioned such that a top surface of the fourth layer is illuminated with an evanescent tail of excitation light guided by the optical waveguide for activating the fluorescent tags when the fluorescent tags are present on top of the fourth layer; and
   a fifth layer located on top of the fourth layer, wherein the fifth layer comprises a microfluidic channel,
   wherein the optical waveguide is configured and positioned such that the microfluidic channel is illuminated with the evanescent tail,
   wherein the rejection filter is positioned such that fluorescence from activated fluorescent tags is filtered before falling onto the detector element,
   wherein the rejection filter is configured to reject a wavelength range of the excitation light,
   wherein the rejection filter is configured to transmit a wavelength range of fluorescence from the activated fluorescent tags,
   wherein the detector element is positioned such that light from the activated fluorescent tags can be received,
   wherein the integrated semiconductor device comprises a cladding layer between the fourth layer and the fifth layer, and
   wherein the integrated semiconductor device comprises a protective layer between the fourth layer and the cladding layer, wherein the protective layer comprises an etch stop layer.

2. The integrated semiconductor device according to claim 1, wherein the detector element is positioned such that light originating from the microfluidic channel can be received.

3. The integrated semiconductor device according to claim 2, wherein the optical waveguide forms a wall of the microfluidic channel.

4. The integrated semiconductor device according to claim 1, wherein the first layer, the second layer, the third layer, and the fourth layer are within a CMOS chip,
   wherein the fifth layer is within a fluidic substrate, and
   wherein the CMOS chip is bonded to the fluidic substrate.

5. The integrated semiconductor device according to claim 1,
   wherein, at a sensing region where interaction between the excitation light and the fluorescent tags is configured to occur, the cladding layer is patterned with a reduced thickness or is locally absent.

6. The integrated semiconductor device according to claim 5, wherein, at the sensing region, the protective layer has been locally removed.

7. The integrated semiconductor device according to claim 1, further comprising:
   a grating coupler optically coupled to the optical waveguide, wherein the grating coupler is configured to couple incoming excitation light into the optical waveguide; and
   a mirror positioned such that incoming excitation light is reflected towards the grating coupler.

8. The integrated semiconductor device according to claim 7,
   wherein the mirror is positioned perpendicular to the direction of the incoming excitation light.

9. The integrated semiconductor device according to claim 1, wherein the detector element comprises a spectral filter positioned such that light from the activated fluorescent tags is filtered before falling onto the detector element.

10. The integrated semiconductor device according to claim 1, further comprising a non-continuous metal layer positioned in between the second layer and the fourth layer, wherein the non-continuous metal layer comprises a gap positioned to allow light from the activated fluorescent tags to reach the detector element.

11. The integrated semiconductor device according to claim 10, wherein the non-continuous metal layer is optically absorbent.

12. The integrated semiconductor device-according to claim 1, further comprising at least one baffle positioned such that light from the activated fluorescent tags is redirected towards the detector element.

13. The integrated semiconductor device according to claim 12, wherein the at least one baffle is optically absorbent.

14. The integrated semiconductor device according to claim 12, wherein the at least one baffle is a cavity.

15. The integrated semiconductor device according to claim 1, wherein the optical waveguide is passivated with $Al_2O_3$ for reducing scattering of the optical waveguide.

16. The integrated semiconductor device according to claim 1, further comprising a biological layer configured to bind particles of interest, wherein the biological layer is located on top of the fourth layer.

17. The integrated semiconductor device according to claim 1, wherein the rejection filter comprises a Bragg filter.

18. The integrated semiconductor device according to claim 1, further comprising a nano-sized hole through the fifth layer down to the fourth layer, wherein the nano-sized hole comprises means for translocating a biomolecule.

19. A microchip comprising a plurality of integrated semiconductor devices for detecting fluorescent tags, wherein each integrated semiconductor device comprises:
   a first layer, wherein the first layer comprises a detector element;
   a second layer located on top of the first layer, wherein the second layer comprises a rejection filter;
   a third layer located on top of the second layer, wherein the third layer is fabricated from a dielectric material;
   a fourth layer located on top of the third layer,
   wherein the fourth layer comprises an optical waveguide configured and positioned such that a top surface of the fourth layer is illuminated with an evanescent tail of excitation light guided by the optical waveguide for activating the fluorescent tags when the fluorescent tags are present on top of the fourth layer, wherein the optical waveguide comprises a single mode waveguide, and wherein a grating coupler is optically coupled to the single mode waveguide; and a fifth layer located on top of the fourth layer, wherein the fifth layer comprises a microfluidic channel, wherein the optical waveguide is configured and positioned such that the microfluidic channel is illuminated with the evanescent tail, wherein the rejection filter is positioned such that fluorescence from activated fluorescent tags is filtered before falling onto the detector element, wherein the rejection filter is configured to reject a wavelength range of the excitation light, wherein the rejection filter is configured to transmit a wavelength range of fluorescence from the activated fluorescent tags, and wherein the detector element is positioned such that light from the activated fluorescent tags can be received.

20. An integrated semiconductor device for detecting fluorescent tags, comprising:

a first layer, wherein the first layer comprises a detector element;

a second layer located on top of the first layer, wherein the second layer comprises a rejection filter;

a third layer located on top of the second layer, wherein the third layer is fabricated from a dielectric material;

a fourth layer located on top of the third layer, wherein the fourth layer comprises an optical waveguide configured and positioned such that a top surface of the fourth layer is illuminated with an evanescent tail of excitation light guided by the optical waveguide for activating the fluorescent tags when the fluorescent tags are present on top of the fourth layer, and wherein the optical waveguide is optically coupled to a multimode waveguide via a taper; and a fifth layer located on top of the fourth layer, wherein the fifth layer comprises a microfluidic channel, wherein the optical waveguide is configured and positioned such that the microfluidic channel is illuminated with the evanescent tail, wherein the rejection filter is positioned such that fluorescence from activated fluorescent tags is filtered before falling onto the detector element, wherein the rejection filter is configured to reject a wavelength range of the excitation light, wherein the rejection filter is configured to transmit a wavelength range of fluorescence from the activated fluorescent tags, and wherein the detector element is positioned such that light from the activated fluorescent tags can be received.

* * * * *